(12) United States Patent
Koyama et al.

(10) Patent No.: US 9,217,428 B2
(45) Date of Patent: Dec. 22, 2015

(54) TUBING PUMP FOR DELIVERING FLUID IN A TUBE

(71) Applicants: Namiki Precision Singapore Pte. Ltd., Singapore (SG); Namiki Seimitsu Houseki Kabushiki Kaisha, Tokyo (JP)

(72) Inventors: Masahiro Koyama, Singapore (SG); Makoto Kashiwagi, Tokyo (JP)

(73) Assignees: Namiki Precision Singapore Pte. Ltd., Singapore (SG); Namiki Seimitsu Houseki Kabushiki Kaisha, Tokyo (JP)

(*) Notice: Subject to any disclaimer, the term of this patent is extended or adjusted under 35 U.S.C. 154(b) by 17 days.

(21) Appl. No.: 13/760,794

(22) Filed: Feb. 6, 2013

(65) Prior Publication Data

US 2014/0219843 A1 Aug. 7, 2014

(51) Int. Cl.
*F04B 43/08* (2006.01)
*F04B 45/08* (2006.01)
*A61M 1/10* (2006.01)
*A61M 5/142* (2006.01)

(52) U.S. Cl.
CPC ............ *F04B 45/08* (2013.01); *A61M 1/1039* (2014.02); *F04B 43/08* (2013.01); *A61M 5/142* (2013.01)

(58) Field of Classification Search
CPC ...... F04B 43/08; F04B 43/084; A61M 5/142; A61M 1/1037; A61M 1/1039; A61M 1/1046
USPC .............. 417/477.3, 477.9, 477.11, 478
See application file for complete search history.

(56) References Cited

U.S. PATENT DOCUMENTS

| | | | | | |
|---|---|---|---|---|---|
| 2,412,397 | A | * | 12/1946 | Harper | 417/474 |
| 2,689,530 | A | * | 9/1954 | Harvey | 417/474 |
| 3,471,079 | A | * | 10/1969 | Myers | 417/397 |
| 3,606,596 | A | * | 9/1971 | Edwards | 417/479 |
| 5,151,019 | A | * | 9/1992 | Danby et al. | 417/474 |
| 7,998,121 | B2 | * | 8/2011 | Stringham | 604/250 |
| 8,382,447 | B2 | * | 2/2013 | Wang et al. | 417/53 |
| 8,545,197 | B2 | * | 10/2013 | Caramuta | 417/477.2 |

* cited by examiner

*Primary Examiner* — Devon Kramer
*Assistant Examiner* — Nathan Zollinger
(74) *Attorney, Agent, or Firm* — Studebaker & Brackett PC

(57) ABSTRACT

A tubing pump capable of improving flow rate accuracy which is required, particularly, in infusion pumps for medical use is developed. In a tubing pump that delivers a liquid in a tube which is separately loaded, a pump mechanism includes a valve mechanism unit that occludes and releases occlusion to the loaded tube and a tube pressing mechanism unit that repeatedly presses the tube, and the tube squeezing mechanism unit includes a pump block which has its movement guided by at least two guide shafts.

3 Claims, 10 Drawing Sheets

TUBING PUMP FOR DELIVERING FLUID IN A TUBE

BACKGROUND OF THE INVENTION

1. Field of the Invention

The present invention relates to a tubing pump that is primarily used as an infusion pump for medical use and that delivers fluid in a tube, which is separately loaded into a pumping mechanism.

2. Description of the Related Art

In the related art, infusion pumps for medical use include a reciprocating type infusion pump in which a tube is loaded between two V-grooves and is repeatedly pressed by a reciprocation of any one of the two V-grooves.

As an example of the reciprocating type infusion pump, Patent Document 1 discloses a reciprocating type infusion pump in which a tube is loaded between a V-groove formed by an upper jaw 220, a lower jaw 222 and a V-groove of a shuttle 200 and is repeatedly pressed by a reciprocation of the shuttle 200.

In the infusion pump disclosed in Patent Document 1, an upstream valve 412 is positioned on the upstream side of the shuttle 200, and a downstream valve 414 is positioned on the downstream side thereof.

The upstream valve 412 and the downstream valve 414 occlude a tube or open the tube at an appropriate timing in association with the reciprocation of the shuttle 200, and thus, fluid in the infusion tube is transferred.

Operational ranges of the shuttle 200, the upstream valve 412, and the downstream valve 414 are defined by a cam 100 with cam profiles that define the operational of the shuttle 200, the upstream valve 412, and the downstream valve 414.

Another example of a reciprocating type infusion pump, Patent Document 2 discloses a reciprocating type infusion pump in which a tube is loaded between a V-groove of a V-groove-shaped fixed component 22 and a V-groove-shaped driving component 12A and is repeatedly pressed by the reciprocation action of the V-groove-shaped driving component 12A.

The reciprocating type infusion pumps as disclosed in Patent Document 1 and Patent Document 2 produce an accurate flow rate accuracy as compared with, for example, a peristaltic-type infusion pump disclosed in Patent Document 3 in which an tube is pressed by peristalsis of all of a plurality of fingers.

However, further improvement of flow rate accuracy, particularly in infusion pumps for medical use is required.

(Patent Document 1) Japanese Laid-Open Patent Publication No. hei 11-508017

(Patent Document 2) International Patent Publication No. WO2009/133705

(Patent Document 3) Japanese Laid-Open Patent Publication No. hei 5-277183

SUMMARY OF THE INVENTION

According to an aspect of the present invention, there is provided a tubing pump that delivers fluid in a tube, which is separately loaded into a pump mechanism. The pump mechanism includes: a valve mechanism unit that occluded and opens the loaded tube, and a tube pressing mechanism unit that repeatedly presses the tube, the tube pressing mechanism unit included a pump block that is movable along at least two guided shafts, and the tube being is repeatedly pressed by a continuous reciprocation of the pump block.

According to the above configuration, since the movement of the driving unit can be prevented, fluid in a tube may be transferred at further stable flow rate accuracy.

In another aspect of this present invention, the tube pressing mechanism unit consist of a front facing component which does not move when delivering the liquid in the tube, the front facing component is being assembled at a position directly opposite to the pump block. The first groove profile with an approximate V shape is formed in the pump block. The second groove profile having an approximately V shape is formed in the front facing component. The tube is repeatedly pressed between the first groove profile and the second groove profile when the pump block reciprocates continuously.

According to the above configuration that allows the process of repeatedly pressing the tube, the deformation state of the tube from squeezing the tube may be restored before the tube is pressed again, thus, the liquid in the tube may be transferred at an accurate flow rate.

According to another aspect of the present invention, the valve mechanism unit is positioned on the upstream side and the downstream side. The tube pressing mechanism unit is positioned between the valve mechanism unit on the upstream side and the valve mechanism unit on the downstream side. The operational range of the pump block assembled in the tube pressing mechanism unit is determined by a pump cam. The operational range of the upstream side valve of the valve mechanism unit is determined by a first valve cam. The operational range of a downstream side valve of the valve mechanism unit is determined by a second valve cam. The pump cam, the first valve cam, and the second valve cam are different cam components to each other.

According to the above configuration, the opening and closing timings of the valve may be setup further to deliver fluid at an accurate flow rate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
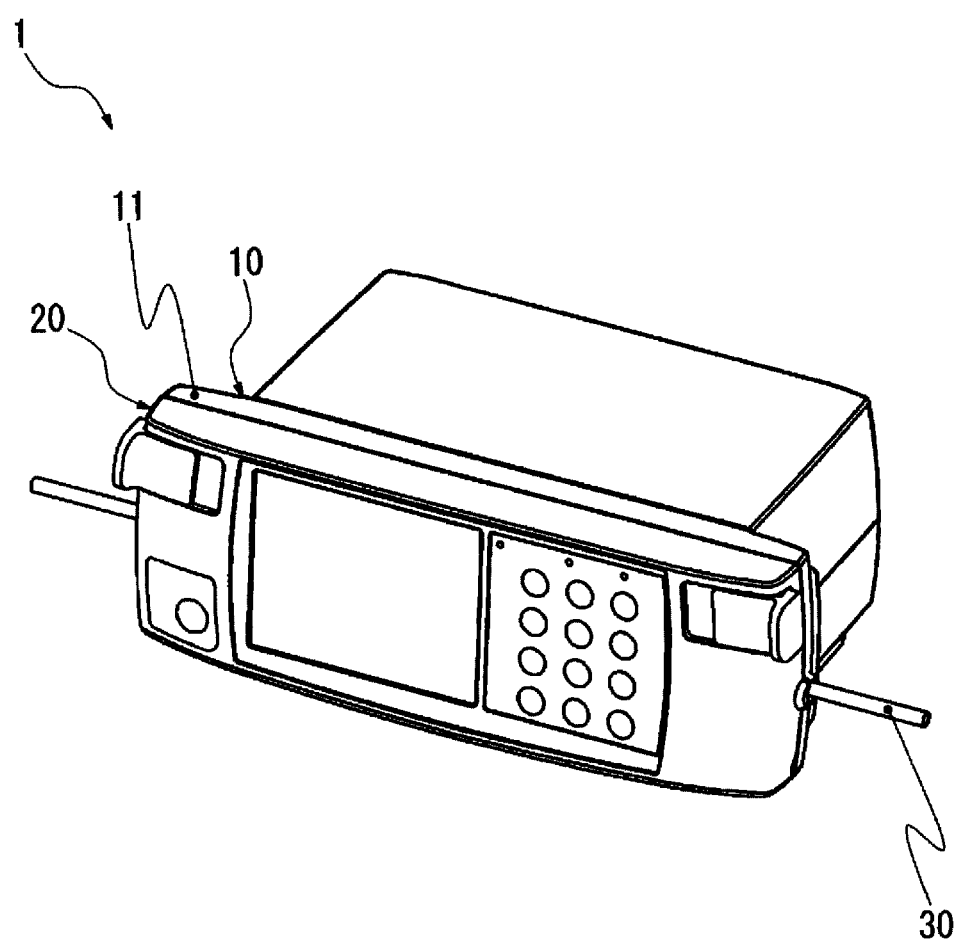
FIG. 1 is a perspective view showing an appearance of an tubing pump according to the present invention.

Hereinafter, an embodiment of the present invention will be described in detail with reference to the accompanying drawings. In addition, the embodiment corresponds to the drawings of FIGS. 1 to 8. In the following description, reference numerals are used to describe elements when there is any appropriate drawing to reference to.

Embodiment

Figure 2:
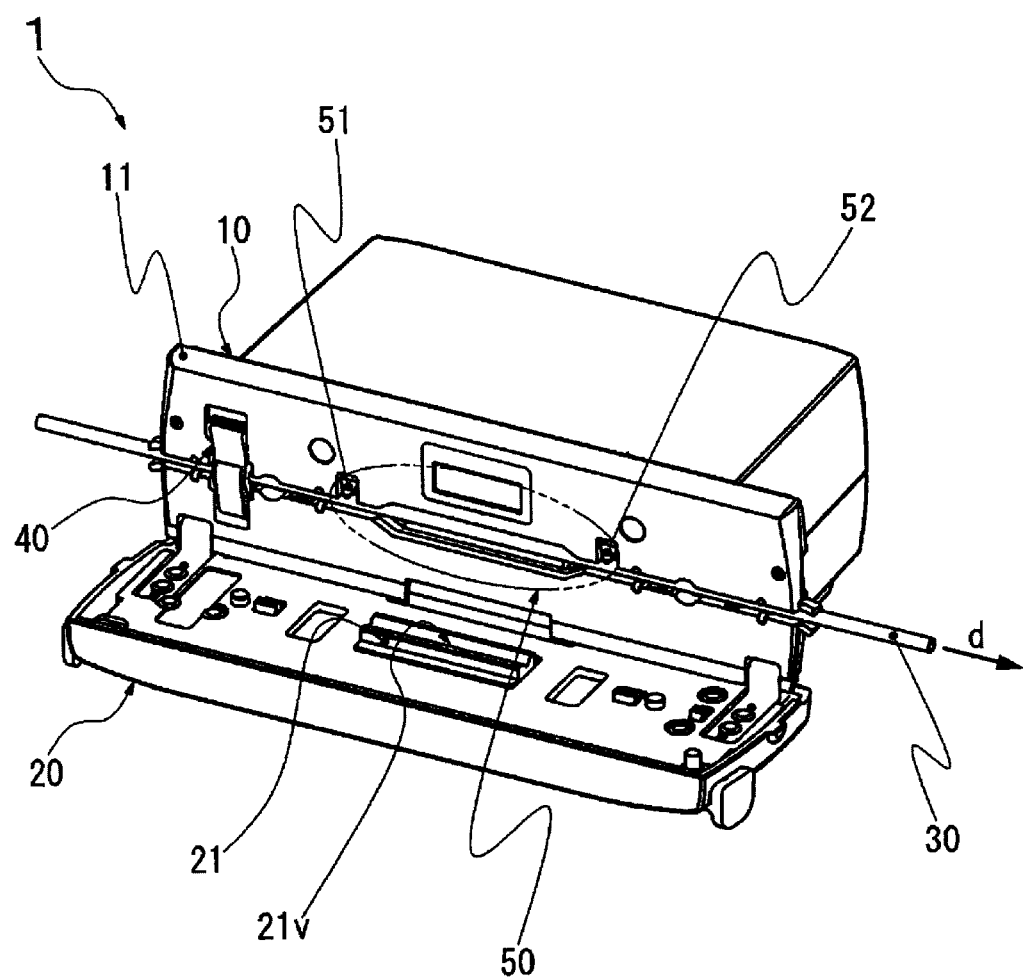
FIG. 2 is a perspective view showing a state where a front door of the tubing pump according to the present invention is opened.

FIGS. 1 and 2 show an appearance of an tubing pump 1 to which a pump mechanism according to the present invention is applied, wherein the tubing pump 1 is an apparatus that forces a fluid (for example, a medicinal fluid or a nutritional agent) in a tube to flow through the pump in a controlled way so as to infuse into a patient's body. The tubing pump 1 includes a door 20 that opens and closes at the front portion of a pump body 10. FIG. 1 shows a closed state of the door 20, and FIG. 2 shows an opened state of the door 20.

The pump body 10 is shaped approximately like a rectangular box shape. The pump body 10 has a horizontal base 11 that has a door in front that can be opened and closed an tube 30 that is clamped by a clamping device 40 that is laterally inserted into base 11 (see FIG. 2). The clamped state of the tube 30 by the clamping device 40 is released when the door 20 is closed.

The horizontal base 11 is the shape of a deep tray and it accommodates the pump mechanism 50 that forcibly transfers the fluid in the loaded tube 30. The pump mechanism 50 forcibly transfers the fluid in the tube 30 from the upstream side to the downstream side, i.e., in the direction d, by sequentially combining a pressing and opening operational to the loaded tube 30, an opening-closing operational of a valve 51 on the upstream side thereof, an opening-closing operational of a valve 52 on the downstream side thereof, and the like (see FIG. 2).

<Configuration of Pump Mechanism>

Figure 3:
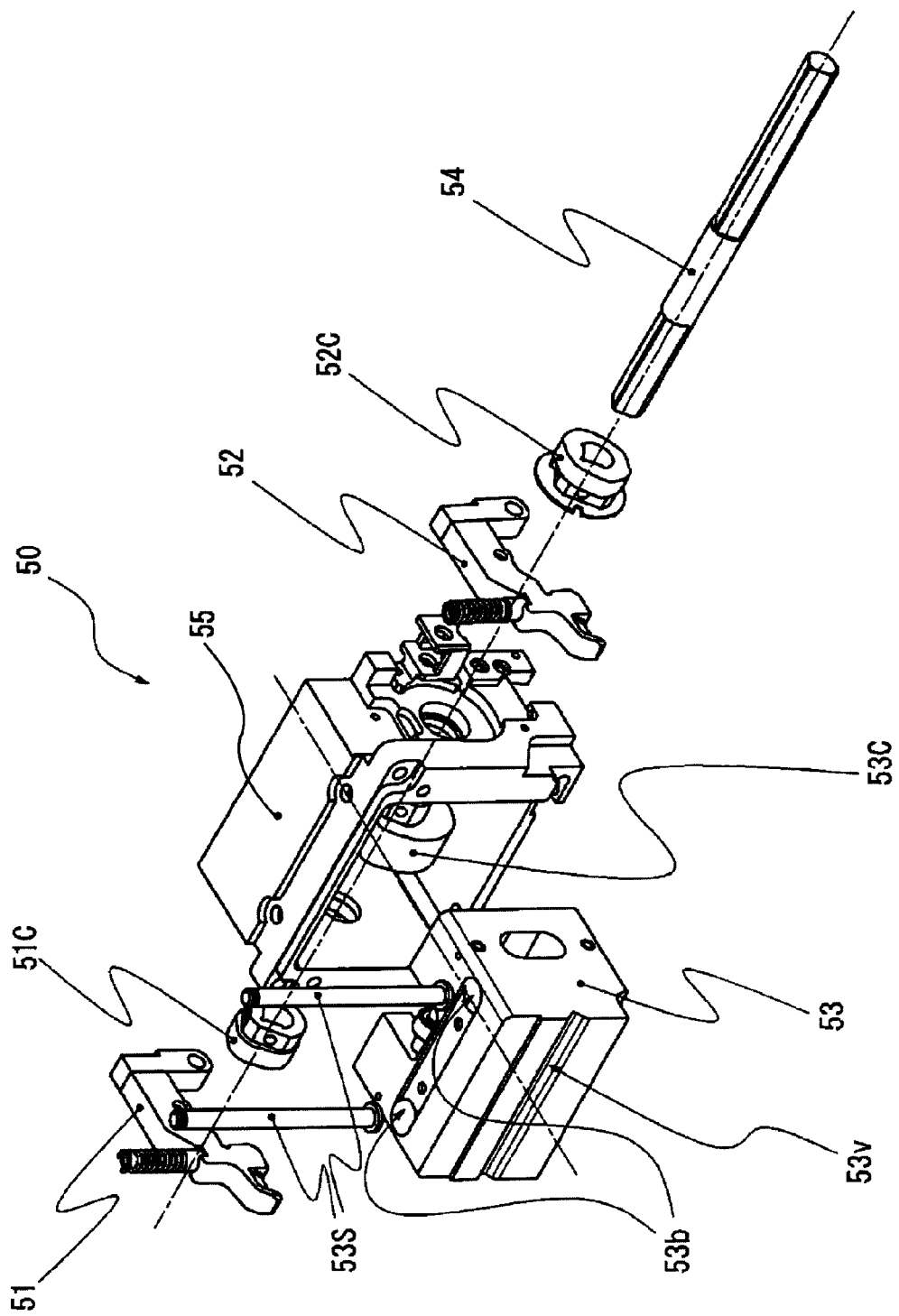
FIG. 3 is an exploded perspective view showing a structure of the tubing pump according to the present invention.

FIG. 3 is an exploded perspective view showing components of the pump mechanism 50. The pump mechanism 50 includes the upstream side valve 51, an upstream side valve cam 51C, the downstream side valve 52, a downstream side valve cam 52C, a pump block 53, a pump block cam 53C, a guide shaft 53S, a shaft 54, a pump block case 55, and the like.

Among these components, the tube pressing mechanism unit is formed by the pump block 53, the pump block cam 53C, and the guide shaft 53S as main components.

The upstream side valve mechanism unit is formed in the pump mechanism 50 by including the upstream side valve 51 and the upstream side valve cam 51C as main components. A downstream side valve mechanism unit is formed in the pump mechanism 50 by including the downstream side valve 52 and the downstream side valve cam 52C as main components.

The upstream side valve cam 51C, the downstream side valve cam 52C, and the pump block cam 53C are fixed to the shaft 54. The shaft 54 continuously rotates by using an electric motor (not shown) as a power source.

When the shaft 54 continuously rotates, the upstream side valve cam 51C, the downstream side valve cam 52C, and the pump block cam 53C respectively cause the upstream side valve 51, the downstream side valve 52, and the pump block 53 to reciprocate in ranges that are predetermined by the respective cam profiles.

At the same time, the tube squeezing mechanism unit function in association with the upstream and downstream side valve mechanism units so as to repeatedly squeeze the infusion tube 30 at an appropriate timing, and also to occlude the infusion tube 30 or open the infusion tube 30 on the upstream side and the downstream side. Hence, the fluid in the infusion tube 30 is transferred.

<Tube Squeezing Mechanism Unit>

As described above, the tube pressing mechanism unit includes the pump block 53, the pump block cam 53C, and the guide shaft 53S.

The position of the pump block 53 that vertically reciprocates is determined by the position of the pump block cam 53C that is fixed to the rotating shaft 54 which causes the cam to rotate.

Figure 4A:
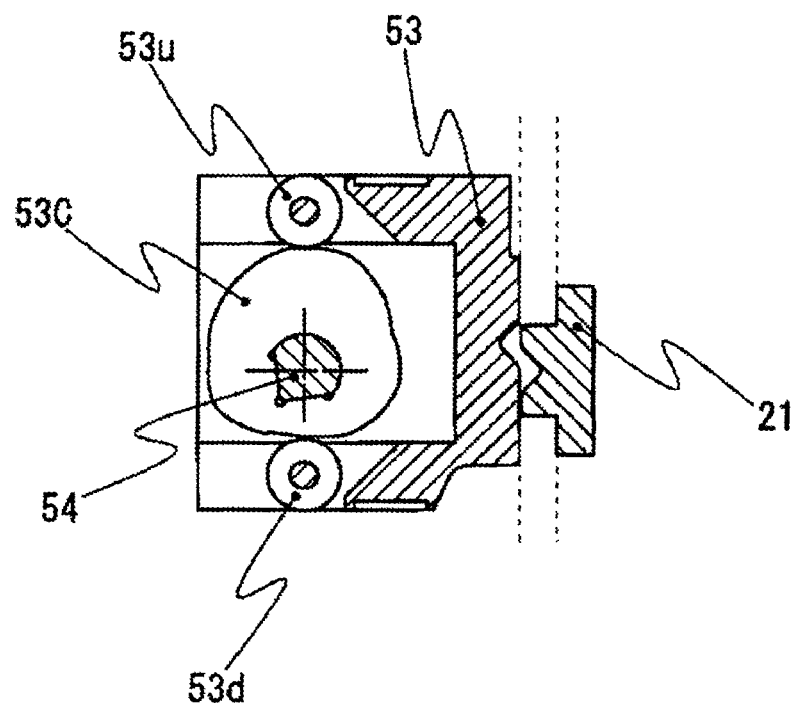
FIGS. 4A to 4C are diagrams showing a positional relationship between a pump cam and a pump block in the tubing pump according to the present invention.
Figure 4B:
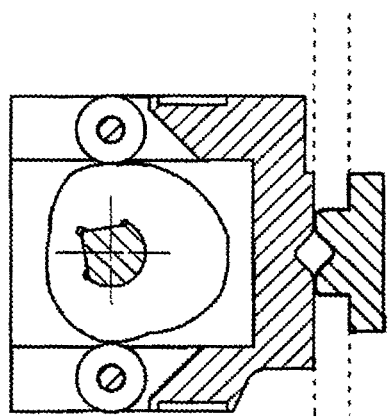
Figure 4C:
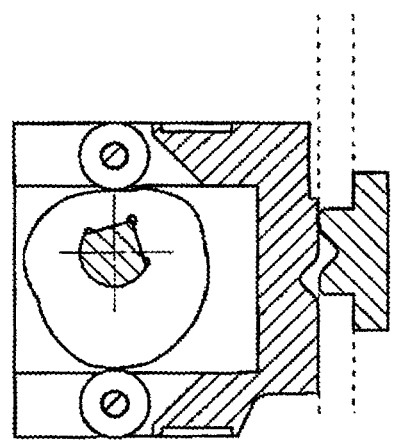

FIGS. 4A to 4C show the cam profile of the pump block cam 53C. The position of the pump block 53 is determined by the position at which the cam surface of the pump block cam 53C having the cam profile shown in FIGS. 4A and 4C contacts with the upper bearing unit 53u or the lower bearing unit 53d of the pump block 53 when the pump block 53 moves vertically from the immediate position where the pump block 53 is located.

FIG. 4A shows a positional relationship between the pump block 53 and the pump block cam 53C in a situation where the pump block 53 is located at the uppermost position.

FIG. 4B shows a positional relationship between the pump block 53 and the pump block cam 53C in a situation where the pump block 53 is located at the intermediate position.

FIG. 4C shows a positional relationship between the pump block 53 and the pump block cam 53C in a situation where the pump block 53 is located at the lowermost position.

In addition, the pump block 53 is guided and move vertically using guide shafts 53S that pass through the ball bushing units 53b located on the upstream side and the downstream side.

The pump block 53 is held by the guide shaft 53S, and thus the pump block 53 may be restricted from moving in other directions when the pump block 53 vertically reciprocates.

In addition, the pump block 53 is restricted from moving in other directions, thereby allowing vibration and noise generated during the operational of the tubing pump 1 to be controlled and contributing to the flow rate accuracy of the infusion pump.

A V-groove 53v, which is a concave area having an approximately V shape, is formed in the pump block 53, and the infusion tube 30 is loaded along the V-groove 53v.

The pump block's front facing component 21 is fixed to the door 20 at a position opposite to the pump block 53 when the door 20 is closed.

Figure 6A:
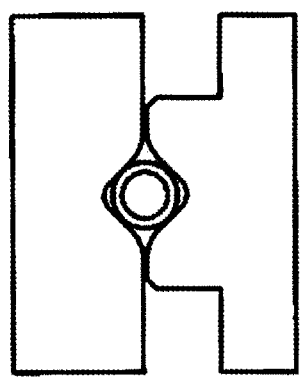
FIGS. 6A to 6D are schematic diagrams showing a deformation and restoration state of a tube in the tubing pump according to the present invention.
Figure 6B:
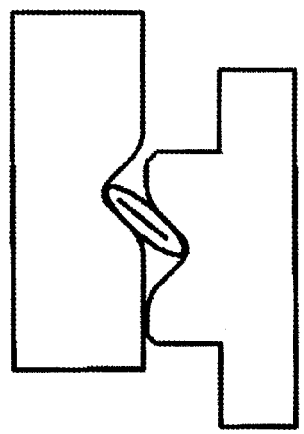
Figure 6C:
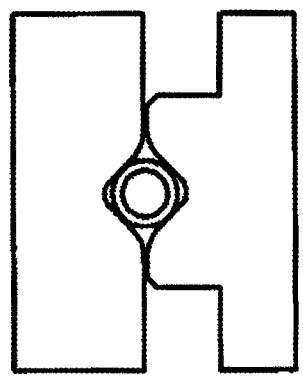

The tube 30 is loaded in a diamond-shaped space formed by the V-groove 21v which has a concave area with an approximate V shape on the pump block's front facing component 21 and the V-groove 53v of the pump block 53 that is opposite to each other (see FIGS. 6A and 6C).

Figure 6D:
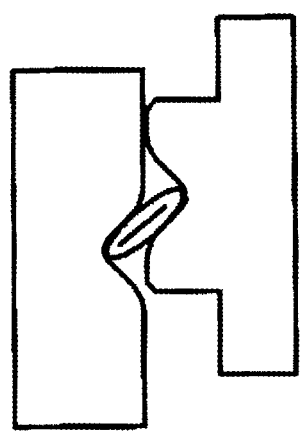

From this setup, when the pump block 53 vertically reciprocates, the tube 30 is repeatedly pressed (see FIGS. 6B and 6D).

When the diamond-shaped space is formed again upon released from a state (FIG. 6B) where the tube 30 is squeezed during the operational of the pump block 53, the shape of the tube 30 tries to return to its state prior to being squeezed by the elastic force of the tube 30 material and also by the pressure of the fluid flowing into the tube 30.

At the same time, the tube 30 is pressed from both sides by the inclined surface of the V-groove 53v and the inclined surface of the V-groove 21v in addition to the tube 30 material's elastic force and the pressure of the fluid. Thus, the shape of tube 30 will be restored.

For this reason, the shape of the tube 30 can be reliably restored every time when tube 30 is pressed. Hence, the transfer amount of the fluid is stable every time the tube 30 is pressed and restored, thereby improving the flow rate accuracy.

<Valve Mechanism Unit>

The valve mechanism unit includes the upstream side valve 51 and the upstream side valve cam 51C on the upstream side, and includes the downstream side valve 52 and the downstream side valve cam 52C on the downstream side.

The function of the valve 51 (52) that occludes the tube 30 and the release of the occlusion of the infusion tube 30 is determined by the profile of the valve cam 51C (52C) that rotates around the rotating shaft 54.

Figure 7A:
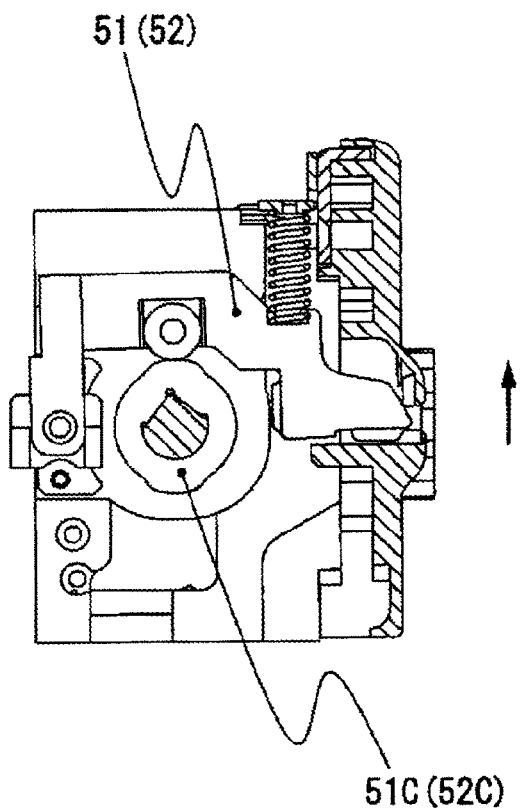
FIGS. 7A and 7B are diagrams showing a positional relationship between a valve cam and a valve in the tubing pump according to the present invention.

FIG. 7A shows the positional relationship between the valve 51 (52) and the valve cam 51C (52C) when the valve 51 (52) is in a state where the valve 51 (52) opens tube 30.

Figure 7B:
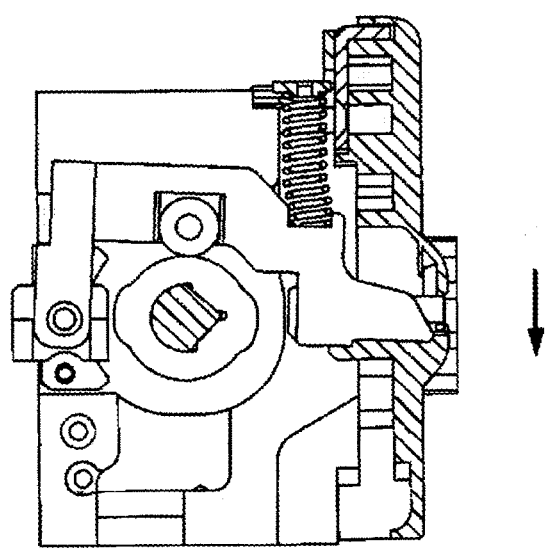

FIG. 7B shows the positional relationship between the valve 51 (52) and the valve cam 51C (52C) when the valve 51 (52) is in a state when the valve 51 (52) occludes tube 30.

Since the upstream side valve 51 and the downstream side valve 52 are separate components, an ideal valve angle may be set by largely forming a movable unit, and thus the flow rate accuracy is improved as the infusion pump is improved.

<Operational Relationship between Pump Block and Valve>

Figure 8:
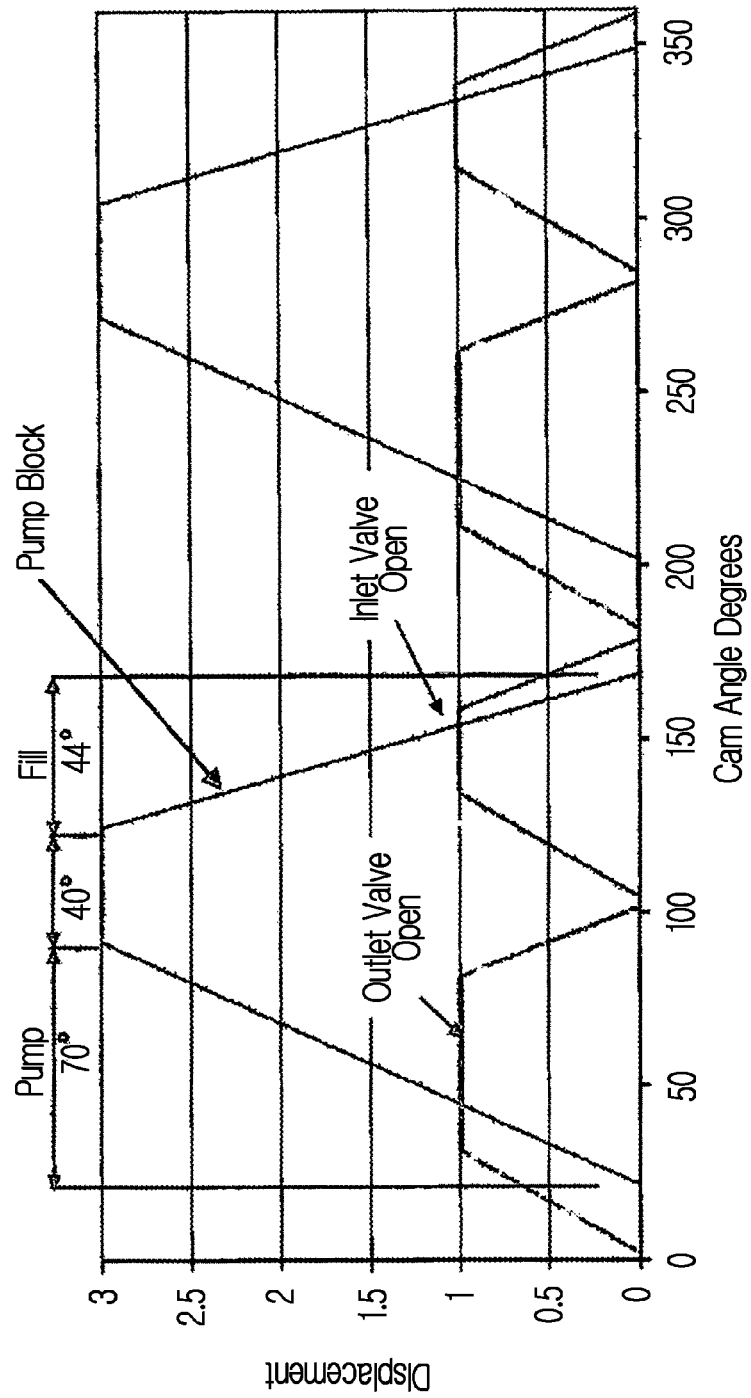
FIG. 8 is a timing chart showing operational timings of the pump block and the valve in the tubing pump according to the present invention.

FIG. 8 is a timing chart showing the operational timings of the pump block 53, the upstream side valve 51, and the downstream side valve 52 when the shaft 54 rotates one revolution in the tubing pump 1 of the present embodiment.

When the shaft 54 rotates one revolution, the pump block 53 vertically reciprocates once.

When the shaft 54 rotates one revolution, the upstream side valve 51 performs an operational of opening and closing the valve twice.

At the same time, the downstream side valve 52 performs the operational for opening and closing the valve twice at timings when the upstream side valve 51 and downstream side valve 52 alternate with each other. FIG. 8 shows the operational relationship between them.

The horizontal axis of FIG. 8 represents the angles at which three different rotating component, that is, the pump block cam 53C, the upstream side valve cam 51C, and the downstream side valve cam 52C, rotate with the shaft 54.

The vertical axis of FIG. 8 represents the displacement of the pump block 53, the upstream side valve 51, and the downstream side valve 52.

As shown in FIG. 8, in the present embodiment, for the valves 51 and 52, the difference between occluded and open is set to a value of 1. For the pump block, each pump cycle from the intermediate or zero position is set to 3.

Figure 5:
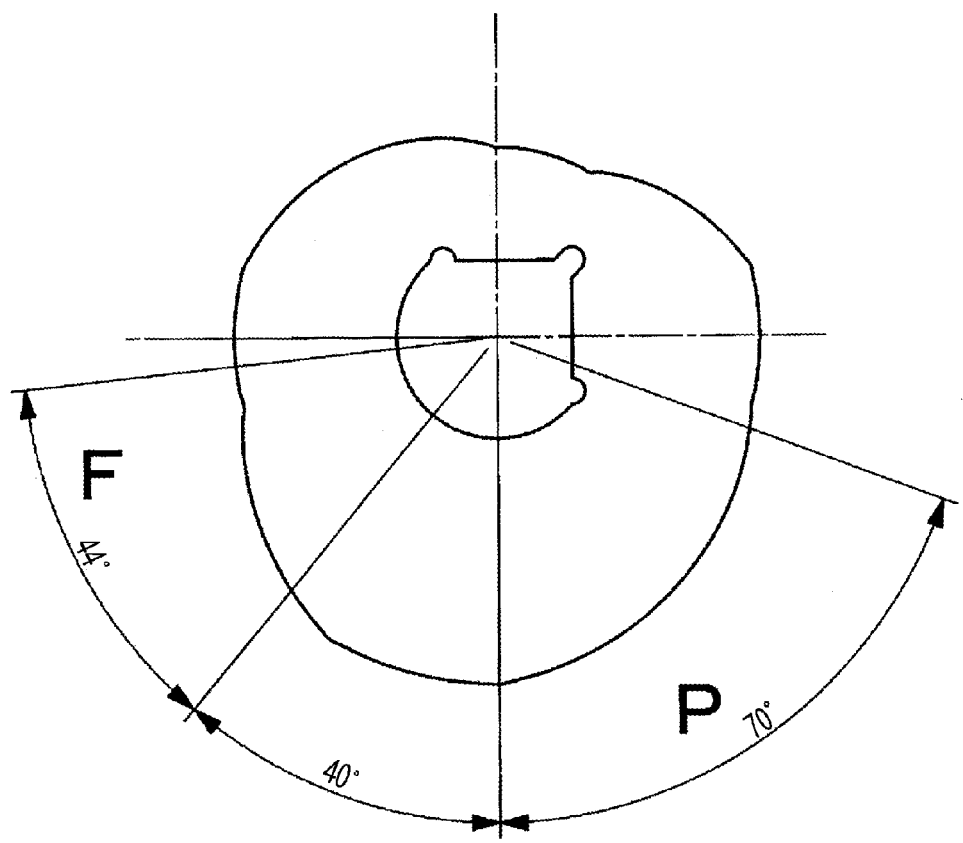
FIG. 5 is a diagram showing a cam profile of the pump cam in the tubing pump according to the present invention.

When the fluid in the infusion tube 30 is sucked (filled), the pump block cam 53C brings the pump block 53 into operational at the range of 44° indicated as "F" in FIG. 5. At this range, the upstream side valve 51 opens the infusion tube 30, and the downstream side valve 52 occludes the infusion tube 30. As the pump block 53 further moves toward the intermediate position, the fluid is sucked (filled).

When the fluid in the tube 30 is discharged (pumped), the pump block cam 53C brings the pump block 53 into operational at the range of 70° indicated as "P" in FIG. 5. At range, the upstream side valve 51 occludes the infusion tube 30, and the downstream side valve 52 release the occlusion on the infusion tube 30. The fluid is discharged by the inclined surface of the V-groove 53v of the pump block 53 to press the infusion tube 30.

One of the elements for increasing the flow rate accuracy of the infusion pump is to increase the proportion of discharging time as much as possible after considering various conditions such as the opening and closing timings of the valve or elastic force of the tube.

It is necessary to set a wide cam angle range of the pump block cam 53C for discharging (pumping). In the related art in which the pumping operational is performed using a driving component for pressing the tube, operating the cam at upstream side valve and operating the cam at the downstream side valve, it is not likely that the cam angle range of the pump block cam 53C can be set larger than 60°.

However, in the present embodiment, different cams are used to change the operational angles of the pump block 53, the upstream side valve 51, and the downstream side valve 52, thus, a wider range can be designed. As a result, the cam angle range may be set to at least 70°.

In addition, according to the above-described embodiment, the cam angle range for discharging (pumping) is set to 70°, and the cam angle range for sucking (filling) is set to 44°. However, different angle ranges can be set to predetermine the opening and closing timings of the upstream and downstream side valves.

Further, according to the above-described embodiment, one shaft 54 is used as a common rotating shaft for the pump block cam 53C, the upstream side valve cam 51C, and the downstream side valve cam 52C. However, individual rotating shafts can be use on all or some of them.

According to the present invention, a tubing pump capable of further improving flow rate accuracy can be configured.

While this invention has been particularly shown and described with reference to exemplary embodiments thereof, it will be understood by those skilled in the art that various changes in form and details may be made therein without departing from the spirit and scope of the invention as defined by the appended claims.

The invention claimed is:

1. A tubing pump that delivers fluid in a tube which is separately loaded, using a pump mechanism, wherein the pump mechanism comprises a valve mechanism unit that occludes the tube and releases occlusion to the tube, and a tube pressing mechanism unit that repeatedly presses the tube, the tube pressing mechanism unit comprises at least two guide shafts which extend substantially perpendicular to an extending direction of the tube located to be pressed in the pump mechanism and a pump block that has its movement guided by the at least two guide shafts in an axial direction of the at least two guide shafts, and the tube is repeatedly pressed by a continuous reciprocation of the pump block, wherein the tube pressing mechanism unit is coupled with
a front facing component which does not operate when delivering the fluid in the tube, the front facing component being positioned directly opposite to the pump block,
a first groove portion having an approximate V shape extending along the tube located to be pressed in the pump mechanism is formed in the pump block,
a second groove portion having an approximate V shape extending along the tube located to be pressed in the pump mechanism is formed in the front facing component, and
the tube is repeatedly pressed between an inclined surface of the first groove portion and an inclined surface of the second groove portion when the pump block reciprocates continuously, the inclined surface of the first groove portion and the inclined surface of the second groove portion facing each other.

2. The tubing pump of claim 1, wherein the valve mechanism unit is located at an upstream side and a downstream side,
the tube pressing mechanism unit is disposed between the valve mechanism unit on the upstream side and the valve mechanism unit on the downstream side, an operational range of the pump block located in the tube pressing mechanism unit is determined by a pump cam, an operational range of an upstream side valve of the valve mechanism unit on the upstream side is determined by a first valve cam, an operational range of a downstream side valve of the valve mechanism unit on the downstream side is determined by a second valve cam, and the pump cam, the first valve cam, and the second valve cam are different cam components to each other.

3. The tubing pump of claim 1, wherein the tube pressing mechanism unit has a shaft configured to continuously rotate and a pump cam fixed to the shaft and configured to determine an operational range of the pump block, and the pump cam is formed such that the tube pressing mechanism unit occludes the tube twice during one revolution of the shaft.

* * * * *